(12) United States Patent
Pickett et al.

(10) Patent No.: US 7,674,844 B2
(45) Date of Patent: *Mar. 9, 2010

(54) LABELLED BEADS

(75) Inventors: Nigel Pickett, London (GB); Andrew James Sutherland, Kidderminster (GB)

(73) Assignee: Nanoco Technologies Limited, Manchester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/432,274

(22) Filed: Apr. 29, 2009

(65) Prior Publication Data

US 2009/0263816 A1  Oct. 22, 2009

Related U.S. Application Data (63) Continuation of application No. 11/784,174, filed on Apr. 5, 2007, now Pat. No. 7,544,725.

(30) Foreign Application Priority Data

Apr. 5, 2006  (GB) ................. 0606845.6

(51) Int. Cl.
- C08K 9/00 (2006.01)
- C03C 25/26 (2006.01)
- C12Q 1/68 (2006.01)

(52) U.S. Cl. ............ 523/200; 523/202; 523/205; 435/6

(58) Field of Classification Search ......... 523/200, 523/202, 205; 435/6
See application file for complete search history.

(56) References Cited

U.S. PATENT DOCUMENTS

| | | | |
|---|---|---|---|
| 4,609,689 | A | 9/1986 | Schwartz et al. |
| 6,114,038 | A | 9/2000 | Castro et al. |
| 6,207,229 | B1 | 3/2001 | Bawendi et al. |
| 6,322,901 | B1 | 11/2001 | Bawendi et al. |
| 6,379,635 | B2 | 4/2002 | O'Brien et al. |
| 6,660,379 | B1 | 12/2003 | Lakowicz et al. |
| 7,544,725 | B2 * | 6/2009 | Pickett et al. ............ 523/200 |
| 2003/0017264 | A1 | 1/2003 | Treadway et al. |
| 2003/0106488 | A1 | 6/2003 | Huang et al. |
| 2004/0110347 | A1 | 6/2004 | Yamashita |
| 2007/0104865 | A1 | 5/2007 | Pickett |
| 2007/0202333 | A1 | 8/2007 | O'Brien et al. |
| 2007/0238126 | A1 | 10/2007 | Pickett et al. |
| 2008/0160306 | A1 | 7/2008 | Mushtaq et al. |

(Continued)

FOREIGN PATENT DOCUMENTS

CN  1394599  2/2003

(Continued)

OTHER PUBLICATIONS

Agger, J.R. et al., *J. Phys. Chem. B* (1998) 102, pp. 3345-3353.

(Continued)

*Primary Examiner*—Jezia Riley
(74) *Attorney, Agent, or Firm*—Goodwin Procter LLP (57) ABSTRACT

A labeled polymeric bead wherein individual beads comprise a primary particle formed of a synthetic polymeric material, and at least one secondary particle entrapped within the primary particle of the bead and being comprised of a synthetic polymer material incorporating reporter moieties.

20 Claims, 8 Drawing Sheets

U.S. PATENT DOCUMENTS

2008/0220593 A1 9/2008 Pickett et al.
2008/0257201 A1 10/2008 Harris et al.
2008/0264479 A1 10/2008 Harris et al.

FOREIGN PATENT DOCUMENTS

| GB | 9518910 | 9/1995 |
| --- | --- | --- |
| JP | 2005-139389 | 6/2005 |
| WO | WO-97-010175 | 3/1997 |
| WO | WO-97-10175 | 3/1997 |
| WO | WO-00-17642 | 3/2000 |
| WO | WO-2000-17642 | 3/2000 |
| WO | WO-02/04527 | 1/2002 |
| WO | WO-2002-004527 | 1/2002 |
| WO | WO-02/29140 | 4/2002 |
| WO | WO-2002-029140 | 4/2002 |
| WO | WO-03/099708 | 12/2003 |
| WO | WO-2004-033366 | 4/2004 |
| WO | WO-2004-066361 | 8/2004 |
| WO | WO-2005-021150 | 3/2005 |
| WO | WO-2005-106082 | 11/2005 |
| WO | WO-2006-017125 | 2/2006 |
| WO | WO-2006-116337 | 11/2006 |
| WO | WO-2007-049052 | 5/2007 |
| WO | WO-2007-060591 | 5/2007 |
| WO | WO-2007-065039 | 6/2007 |

OTHER PUBLICATIONS

Aldana, J. et al. "Photochemical Instability of CdSe Nanocrystals Coated by Hydrophilic Thiols", *J. Am. Chem. Soc.* (2001), 123: 8844-8850.

Alivisatos, A.P. "Perspectives on the Physical Chemistry of Semiconductor Nanocrystals", *J. Phys. Chem.*, (1996), 100, pp. 13226-13239.

Arici et al., *Thin Solid Films* 451-452 (2004) 612-618.

Battaglia et al., "Colloidal Two-dimensional Systems: CdSe Quantum Shells and Wells", *Angew Chem.* (2003) 42:5035-5039.

Bawendi, M.G. "The Quantum Mechanics of Larger Semiconductor Clusters ("Quantum Dots")", *Annu. Rev. Phys. Chem.* (1990), 42: 477-498.

Berry, C.R. "Structure and Optical Absorption of AgI Microcrystals", *Phys. Rev.* (1967) 161: 848-851.

Bunge, S.D. et al. "Growth and morphology of cadmium chalcogenides: the synthesis of nanorods, tetrapods, and spheres from CdO and $Cd(O_2CCH_3)_2$", *J. Mater. Chem.* (2003) 13:1705-1709.

Castro et al., "Synthesis and Characterization of Colloidal $CuInS_2$ Nanoparticles from a Molecular Single-Source Precursors", *J. Phys. Chem. B* (2004) 108:12429.

Chun et al., *Thin Solid Films* 480-481 (2005) 46-49.

Contreras et al., "ZnO/ZnS(O,OH)/Cu(In,Ga)Se$_2$/Mo Solar Cell with 18:6% Efficiency," from 3d World Conf. on Photovol. Energy Conv., *Late News Paper* (2003) pp. 570-573.

Cui et al., "Harvest of near infrared light in PbSe nanocrystal-polymer hybrid photovoltaic cells," *Appl. Phys. Lett.* 88 (2006) 183111-183111-3.

Dance et al., *J. Am. Chem. Soc.* (1984) 106:6285-6295.

Daniels et al., "New Zinc and Cadmium Chalcogenide Structured Nanoparticles," *Mat. Res. Soc. Symp. Proc.* 789 (2004) pp. 31-36.

Eychmüller, A. et al. "A quantum dot quantum well: CdS/HgS/CdS", *Chem. Phys. Lett.* 208, pp. 59-62 (1993).

Fendler, J.H. et al. "The Colloid Chemical Approach to Nanostructured Materials", *Adv. Mater.* (1995) 7: 607-632.

Gao, M. et al. "Synthesis of PbS Nanoparticles in Polymer Matrices", *J. Chem. Soc. Commun.* (1994) pp. 2779-2780.

Gou et al., *J. Am. Chem. Soc.* (2006) 128:7222-7229.

Gur et al., "Air stable all-inorganic nanocrystal solar cells processed from solution," *Lawrence Berkeley Natl. Lab., University of California*, paper LBNL-58424 (2005).

Gurin, *Colloids Surf. A* (1998) 142:35-40.

Guzelian, A. et al. "Collodial chemical synthesis and characterization of InAs nanocrystal quantum dots", *Appl. Phys. Lett.* (1996) 69: 1432-1434.

Guzelian, A. et al., "Synthesis of Size-Selected, Surface-Passivated InP Nanocrystals", *J. Phys. Chem.* (1996) 100: 7212-7219.

Hagfeldt, A. et al. "Light-induced Redox Reactions in Nanocrystalline Systems", *Chem. Rev.* (1995) 95: 49-68.

Henglein, A. "Small-Particle Research: Physicochemical Properties of Extremely Small Colloidal Metal and Semiconductor Particles", *Chem Rev.* (1989) 89: 1861-1873.

Hirop et al., "Synthesis of Mixed Copper-Indium Chalcogenolates. Single-Source Precursors for the Photovoltaic Materials $CuInQ_2$ (Q =S, Se)," *J. Am. Chem. Soc.* (1993) 115:1597.

Hu et al., "Hydrothermal preparation of $CuGaS_2$ crystallites with different morphologies", *Sol. State Comm.* (2002) 121:493-496.

International Search Report for PCT/GB2005/001611 mailed Sep. 8, 2005 (5 pages).

Jegier, J.A. et al. "Poly(imidogallane): Synthesis of a Crystalline 2-D Network Solid and Its Pyrolysis To Form Nanocrystalline Gallium Nitride in Supercritical Ammonia", *Chem. Mater.* (1998) 10: 2041-2043.

Kaelin et al., "CIS and CIGS layers from selenized nanoparticles precursors," *Thin Solid Films* 431-432 (2003) pp. 58-62.

Kapur et al., "Non-Vacuum processing of $CuIn_{1-x}Ga_xSe_2$ solar cells on rigid and flexible substrates using nanoparticle precursor inks," *Thin Solid Films* 431-432 (2003) pp. 53-57.

Kher, S. et al. "A Straightforward, New Method for the Synthesis of Nanocrystalline GaAs and GaP", *Chem. Mater.* (1994) 6: 2056-2062.

Kim et al., "Synthesis of $CuInGaSe_2$ Nanoparticles by Low Temperature Colloidal Route", *J. Mech. Sci. Tech.* (2005) 19: 2085-2090.

Law et al., "Nanowire dye-sensitized solar cells," *Nature Mater.* (2005) vol. 4 pp. 455-459.

Li et al., *Adv. Mat.* (1999) 11:1456-1459.

Lieber, C. et al. "Understanding and Manipulating Inorganic Materials with Scanning Probe Microscopes", *Angew. Chem. Int. Ed. Engl.* (1996) 35: 687-704.

Little et al., "Formation of Quantum-dot quantum-well heteronanostructures with large lattice mismatch: Zn/CdS/ZnS," 114 *J. Chem. Phys.* 4 (2001).

Lu et al., *Inorg. Chem.* (2000) 39:1606-1607.

LØver, T. et al. "Preparation of a novel CdS nanocluster material from a thiophenolate-capped CdS cluster by chemical removal of SPh ligands", *J. Mater. Chem.* (1997) 7(4): 647-651.

Malik et al., *Adv. Mat.*, (1999) 11:1441-1444.

Matijevic, E. "Monodispersed Colloids: Art and Science", *Langmuir* (1986) 2:12-20.

Matijevic, E. "Production of Monodispersed Colloidal Particles", *Ann. Rev. Mater. Sci.* (1985) 15: 483-518.

Mekis, I. et al., "One-Pot Synthesis of Highly Luminescent CdSe/CdS Core-Shell Nanocrystals via Organometallic and "Greener" Chemical Approaches", *J. Phys. Chem. B.* (2003) 107: 7454-7462.

Mews et al., *J. Phys. Chem.* (1994) 98:934-941.

Mićić et al., "Synthesis and Characterization of InP, GaP, and $GaInP_2$ Quantum Dots", *J. Phys. Chem.* (1995) pp. 7754-7759.

Milliron et al., "Electroactive Surfactant Designed to Mediate Electron Transfer between CdSe Nanocrystals and Organic Semiconductors," *Adv. Materials* (2003) 15, No. 1, pp. 58-61.

Patents Act 1977: Search Report under Section 17 for Application No. GB 0719075.4.

Patents Act 1977: Search Report under Section 17 for Application No. GB 0719073.9.

Pradhan, N. et al. "Single-Precursor, One-Pot Versatile Synthesis under near Ambient Conditions of Tunable, Single and Dual Band Flourescing Metal Sulfide Nanoparticles", *J. Am. Chem. Soc.* (2003) 125: 2050-2051.

Qi et al., "Efficient polymer-nanocrystal quantum-dot photodetectors," *Appl. Phys. Lett.* 86 (2005) 093103-093103-3.

Qu, L. et al. "Alternative Routes toward High Quality CdSe Nanocrystals", *Nano Lett.* (2001) vol. 1, No. 6, pp. 333-337.

Robel et al., "Quantum Dot Solar Cells. Harvesting Light Energy with CdSe Nanocrystals Molecularly Linked to Mesoscopic $TiO_2$ Films," *J. Am. Chem. Soc.* (2006) 128: 2385-2393.

Salata, O.V. et al., *Appl. Phys. Letters* (1994) 65 (2) pp. 189-191.

Sercel, P.C. et al. "Nanometer-scale GaAs clusters from organometallic precursors", *Appl. Phys. Letters* (1992) 61: 696-698.

Shultz et al., *J. Elect. Mat.* (1998) 27:433-437.

Steigerwald, M.L. et al. "Semiconductor Crystallites: A Class of Large Molecules", *Acc. Chem. Res.* (1990) 23: 183-188.

Stroscio, J.A. et al. "Atomic and Molecular Manipulation with the Scanning Tunneling Microscope", *Science* (1991), 254: 1319-1326.

Trinidade et al., "A single source approach to the synthesis of CdSe nanocrystallites", *Advanced Materials*, (1996) vol. 8, No. 2, pp. 161-163.

Vayssieres et al., "Highly Ordered $SnO_2$ Nanorod Arrays from Controlled Aqueous Growth", *Angew. Chem. Int. Ed.* (2004) 43:3666-3670.

Wang Y. et al. "PbS in polymers. From molecules to bulk solids", *J. Chem. Phys.* (1987) 87: 7315-7322.

Weller, H. "Colloidal Semiconductor Q-Particles: Chemistry in the Transition Region Between Solid State and Molecules", *Angew. Chem. Int. Ed. Engl.* (1993) 32: 41-53.

Weller, H. "Quantized Semiconductor Particles: A Novel State of Matter for Materials Science", *Adv. Mater.* (1993) 5: 88-95.

Wells, R.L. et al. "Synthesis of Nanocrystalline Indium Arsenide and Indium Phosphide from Indium(III) Halides and Tris(trimethylsilyl)pnicogens. Synthesis, Characterization, and Decomposition Behavior of $I_3In-P(SiMe_3)_3$", *Chem. Mater.* (1995) 7: 793-800.

Xiao et al., *J. Mater. Chem.* (2001) 11:1417-1420.

Yang et al., *Crystal Growth & Design* (2007) 12/2562.

Zhong et al., "A facile route to synthesize chalcopyrite $CuInSe_2$ nanocrystals in non-coordinating solvent", *Nanotechnology* 18 (2007) 025602.

Agger, J.R. et al., *J. Phys. Chem. B* (1998) 102, pp. 3345-3353.

Aldana, J. et al "Photochemical Instability of CdSe Nanocrystals Coated by Hydrophilic Thiols, " *J. Am. Chem. Soc.* (2001), 123: 8844-8850.

Alivisatos, A.P. "Perspectives on the Physical Chemistry of Semiconductor Nanocrystals", *J. Phys. Chem.*, (1996), 100, pp. 13226-13239.

Arici et al., *Thin Solid Films* 451-452 (2004) 612-618.

Battaglia et al., "Colloidal Two-dimensional Systems: CdSe Quantum Shells and Wells," *Angew Chem.* (2003) 42:5035-5039.

Bawendi, M.G. "The Quantum Mechanics of Larger Semiconductor Clusters ("Quantum Dots")", *Annu. Rev. Phys. Chem.* (1990), 42: 477-498.

Berry, C.R. "Structure and Optical Absorption of AgI Microcrystals", *Phys. Rev.* (1967) 161:848-851.

Bunge, S.D. et al. "Growth and morphology of cadmium chalcogenides: the synthesis of nanorods, tetrapods, and spheres from CdO and $Cd(O_2CCH_3)_2$" *J. Mater. Chem.* (2003) 13:1705-1709.

Castro et al., "Synthesis and Characterization of Colloidal $CuInS_2$ Nanoparticles from a Molecular Single-Source Precursors," *J. Phys. Chem. B* (2004) 108:12429.

Castro et al., *Chem. Mater.* (2003) 15:3142-3147.

Chun et al., *Thin Solid Films* 480-481 (2005) 46-49.

Contreras et al., "ZnO/ZnS(O,OH)/Cu(In,Ga)$Se_2$/Mo Solar Cell with 18:6% Efficiency," from 3d World Conf. On Photovol. Energy Conv., *Late News Paper* (2003) pp. 570-573.

Cui et al., "Harvest of near infrared light in PbSe nanocrystal-polymer hybrid photovoltaic cells," *Appl. Physics Lett.* 88 (2006) 183111-183111-3.

Cumberland et al., "Inorganic Clusters as Single-Source Precursors for Preparation of CdSe, ZnSe, and CdSe/ZnS Nanomaterials" *Chemistry of Materials*, 14, pp. 1576-1584 (2002).

Dance et al., *J. Am. Chem. Soc.* (1984) 106:6285-6295.

Daniels et al., "New Zinc and Cadmium Chalcogenide Structured Nanoparticles," *Mat. Res. Soc. Symp. Proc.* 789 (2004) pp. 31-36.

Eychmüller, A. et al. "A quantum dot quantum well: CdS/HgS/CdS", *Chem. Phys. Lett.* 208, pp. 59-62 (1993).

Fendler, J.H. et al. "The Colloid Chemical Approach to Nanostructured Materials", *Adv. Mater.* (1995) 7: 607-632.

Gao, M. et al. "Synthesis of PBS Nanoparticles in Polymer Matrices", *J. Chem. Soc. Commun.* (1994) pp. 2779-2780.

Gou et al., *J. Am. Chem. Soc.* (2006) 128:7222-7229.

Jiang et al., *Inorg. Chem.* (2000) 39:2964-2965.

Kaelin et al., "CIS and CIGS layers from selenized nanoparticle precursors," *Thin Solid Films* 431-432 (2003) pp. 58-62.

Kapur et al., "Non-Vacuum processing of $CuIn_{1-x}Ga_xSe_2$ solar cells on rigid and flexible substrates using nanoparticle precursor inks," *Thin Solid Films* 431-432 (2003) pp. 53-57.

Kher, S. et al. "A Straightforward, New Method for the Synthesis of Nanocrystalline GaAs and GaP", *Chem. Mater.* (1994) 6: 2056-2062.

Kim et al., "Synthesis of $CuInGaSe_2$ Nanoparticles by Low Temperature Colloidal Route", *J. Mech. Sci. Tech.* (2005) 19: 2085-2090.

Law et al., "Nanowire dye-sensitized solar cells," *Nature Mater.* (2005) vol. 4 pp. 455-459.

Li et al., *Adv. Mat.* (1999) 11:1456-1459.

Lieber, C. et al. "Understanding and Manipulating Inorganic Materials with Scanning Probe Microscopes", *Anqew. Chem. Int. Ed. Engl.* (1996) 35: 687-704.

Little et al., "Formation of Quantum-dot quantum-well heteronanostructures with large lattice mismatch: Zn/CdS/ZnS," 114 *J. Chem. Phys.* 4 (2001).

Lu et al., *Inorq. Chem.* (2000) 39:1606-1607.

LØver, T. et al. "Preparation of a novel CdS nanocluster material from a thiophenolate-capped CdS cluster by chemical removal of SPh ligands", *J. Mater. Chem.* (1997) 7(4): 647-651.

Malik et al., *Adv. Mat.*, (1999) 11:1441-1444.

Matijevic, E. "Monodispersed Colloids: Art and Science", *Langmuir* (1986) 2:12-20.

Matijevic, E. "Production of Monodispersed Colloidal Particles", *Ann. Rev. Mater. Sci.* (1985) 15: 483-518.

Mekis, I. et al., "One-Pot Synthesis of Highly Luminescent CdSe/CdS Core-Shell Nanocrystals via Organometallic and "Greener " Chemical Approaches", *J. Phys. Chem. B*. (2003) 107: 7454-7462.

Mews et al., J. Phys. Chem. (1994) 98:934-941.

Mićić et al., "Synthesis and Characterization of InP, GaP, and $GaInP_2$ Quantum Dots", *J. Phys. Chem.* (1995) pp. 7754-7759.

Milliron et al., "Electroactive Surfactant Designed to Mediate Electron Transfer between CdSe Nanocrystals and Organic Semicondictors," *Adv. Materials* (2003) 15, No. 1, pp. 58-61.

Murray, C.B. et al., "Synthesis and Characterization of Nearly Monodisperse CdE (E = S, Se, Te) Semiconductor Nanocrystallites", *J. Am. Chem. Soc.* (1993) 115 (19) pp. 8706-8715.

Nairn et al., *Nano Letters* (2006) 6:1218-1223.

Nazeeruddin et al., "Conversion of Light to Electricity by cis-$X_2$Bis(2,2'bipyridyl-4,4'- dicarboxylate)ruthenium(II) Charge-Transfer Sensitizers (X= Cl–, Br–, I–, CN–, and SCN–) on Nanocrystalline $TiO_2$ Electrodes," *J. Am. Chem. Soc.* (1993) 115:6382-6390.

Nazeeruddin et al., "Engineering of Efficient Panchromatic Sensitizers for Nanocrystalline $TiO_2$-Based Solar Cells," *J. Am. Chem. Soc.* (2001) 123:1613-1624.

O'Brien et al., "The Growth of Indium Selenide Thin Films from a Novel Asymmetric Dialkydiselenocarbamate," 3 *Chem. Vap. Depos.* 4, pp. 2227 (1979).

Olshavsky, M.A., et al. "Organometallic Synthesis of GaAs Crystallites Exhibiting Quantum Confinement", *J. Am. Chem. Soc.* (1990) 112: 9438-9439.

Olson et al., *J. Phys. Chem. C.* (2007) 111:16640-16645).

Patent Act 1977 Search Report under Section 17 for Application No. GB0522027.2 dated Jan. 27, 2006.

Patent Act 1977 Search Report under Section 17 for Application No. GB0723539.3 dated Mar. 27, 2008.

Patents Act 1977: Search Report under Section 17 for Application No. GB 0606845.6 dated Sep. 14, 2006.

Patents Act 1977: Search Report under Section 17 for Application No. GB 0719075.4.

Patents Act 1977: Search Report under Section 17 for Application No. GB0409877.8 dated Oct. 7, 2004.

Patents Act 1977: Search Report under Section17 for Application No. GB 0719073.9.

Peng et al. "Shape control of CdSe nanocrystals", *Nature*, (2000) vol. 404, No. 6773, pp. 59-61.

Peng et al., "Kinetics of II-VI and III-V Colloidal Semiconductor Nanocrystal Growth: "Focusing" os Size Distributions", *J. Am. Chem. Soc.*, (1998) 129: 5343-5344.

Peng et al., "Mechanisms of the Shape Evolution of CdSe Nanocrystals", *J. Am. Chem. Soc.* (2001) 123:1389-1395.

Pradhan, N. et al. "Single-Precursor, One-Pot Versatile Synthesis under near Ambient Conditions of Tunable, Single and Dual Band Flourescing Metal Sulfide Nanoparticles", *J. Am. Chem. Soc.* (2003) 125: 2050-2051.

Qi et al., "Efficient polymer-nanocrystal quantum-dot photodetectors," *Appl. Physics Lett.* 86 (2005) 093103 - 093103-3.

Qu, L. et al. "Alternative Routes toward High Quality CdSe Nanocrystals", *Nano Lett.* (2001) vol. 1, No. 6, pp. 333-337.

Robel et al., "Quantum Dot Solar Cells. Harvesting Light Energy with CdSe Nanocrystals Molecularly Linked to Mesoscopic $TiO_2$ Films," *J. Am. Chem. Soc.* (2006) 128: 2385-2393.

Salata, O.V. et al., *Appl. Phys. Letters* (1994) 65 (2) pp. 189-191.

Sercel, P.C. et al. "Nanometer-scale GaAs clusters from organometallic precursors", *Appl. Phys. Letters* (1992) 61: 696-698.

Yang et al., *Crystal Growth & Design* (2007) 12/2562.

Yu et al., "Polymer Photovoltaic Cells: Enhanced Efficiencies via a Network of Internal Donor-Acceptor Heterojunctions," 270 *Science* 5243 (1995), pp. 1789-1791.

Zhong et al., "A facile route to synthesize chalcopyrite $CuInSe_2$ nanocrystals in noncoordinating solvent", *Nanotechnology* 18 (2007) 025602.

* cited by examiner

(A) OPTICAL ENCODING OF POLYMER BEADS

QUANTUM DOT (3-10 nm) → DISPERSION POLYMERISATION BEADS → SUSPENSION POLYMERISATION BEADS (B)

(I)

(II)

(III)

LABELLED BEADS

CROSS-REFERENCE TO RELATED APPLICATIONS

This application is a continuation of and claims priority to U.S. patent application Ser. No. 11/784,174, which claims priority to and the benefit of United Kingdom Patent Application Serial No. 0606845.6, filed on Apr. 5, 2006; the disclosure of each of these applications is incorporated herein by reference in its entirety.

FIELD OF THE INVENTION

The present invention relates to particles labeled beads incorporating reporter moieties which are useful in a variety of applications for labeling and detection purposes. The term "beads" is used for convenience and is not intended to impose any particular shape limitation. Thus, for example, the beads may be spherical but other configurations are possible.

BACKGROUND OF THE INVENTION

Labeled beads have been used for many years in diagnostics testing, microscope-based assays, flow cytometry-based assays and combinatorial library synthesis. They also have potential to be used in a wide range of applications including biological monitoring, security/anti-counterfeiting, optical coding, biological assays, optical data storage and sensors.

A labeled bead will generally contain a plurality of reporter moieties. The reporter moieties may, for example, be fluorescent species such as fluorescent dyes or a quantum dot. (For the purposes of the present invention a single dye molecule or quantum dot is considered to be a reporter moiety). Further possibilities include the use of magnetic particles and specifically shaped particles as reporter moieties.

Labeled beads may contain different "species" of reporter moieties. Thus, for example, a labeled bead may contain two or more different types of fluorescent dye or two or more different types of quantum dot. Depending on the number of each species present, the bead will provide a particular signal which may in effect be considered to be a "bar-code". Put another way, there will be a first signal from the first species of reporter moiety, a second signal from the second species of reporter moiety etc. In addition the intensity of the signal from the first reporter moiety may be increased or decreased by the presence of the second reporter moiety. The particular combination of signals uniquely identifies the bead.

It will of course be appreciated that labeled beads may be produced with different combinations of reporter moieties so that different types of bead are distinguished by their "barcode" signal.

By way of illustration, such beads may be used for labeling ("tagging") proteins or nucleic acids. Thus molecules of a first type of nucleic acid or protein may be tagged (e.g. by incubation, covalent attachment, adsorption etc.) with labeled beads providing a first barcode signal. Similarly protein or nucleic acid molecules of a second type may be tagged with labeled beads providing a second barcode signal. The tagged protein or nucleic acids may then be admixed and subjected to a particular reaction. The individual barcodes allow the product mixture to be examined (e.g. after a separation procedure) to determine the origin of the tagged molecule in other words which specific reaction sequences the bead has been exposed to or else which known molecule has been attached to the bead).

Most of the bar-coded labeled particle libraries currently available have been produced by encoding beads with different concentrations of fluorescent dyes and/or metal (including magnetic metal) particles. In the case where the moieties are fluorescent dyes, the size of the library is limited by the overlapping excitation and emission spectra of the dyes. There are also limitations on libraries produced using metal particles as the reporter moieties.

Some of the above mentioned disadvantages are overcome by the use of quantum dots as the reporter moieties.

Quantum dots are a subset of nanoparticles that when excited emit light, with quantum yields of between 30-70% and narrow emission bands across the visible spectrum and extending to both the UV and near infrared spectrum. Compared with conventional fluorescent probes (e.g. organic dyes and lanthanides) quantum dots have a number of advantages. Most notably quantum dots absorb light over a wide range of wavelengths so a number of different light-emitting quantum dots can be stimulated using a single light source to produce an output in parallel, a so-called optical barcode. This is in contrast to conventional fluorescent compounds for which (i) their absorption and emission spectra are closely coupled (thus requiring a number of different light sources for multiplexing purposes), and (ii) their emission spectrum is often extremely broad and overlapping with its absorption spectra.

Labeled beads comprised of polymeric particles incorporating quantum dots have been proposed and may be produced, for example, by including the quantum dots in a suspension polymerisation procedure. One example of such a technique is disclosed in WO 2005/021150 (The University of Manchester) which leads to beads having a size of 0.5 microns upwards.

Typically one population of quantum dot is added to a single polymerisation reaction. All polymer particles produced in a batch from a polymerisation reaction will contain statistically approximately the same number of quantum dots with the average number of quantum dots per polymer particle being determined by the reagent ratios selected in the polymerisation procedure.

Since the number of Quantum Dots per particle is relatively similar it is not trivial to distinguish between two different polymer particles produced in the same polymerisation reaction. This is, in some respects, an advantage in that the product of one polymerisation reaction can be made to be detectably different from that of another polymerisation reaction so the two batches can be used as different labeled beads. However this approach means that one polymerisation reaction produces one batch of optically coded polymer particles. By extension, to generate for example ten differently encoded beads would require ten different polymerisation reactions. For utility in optically encoded systems a large number of encoded microbeads are required which in turn would require a large number of polymerisation reactions to be carried out.

In order to overcome this disadvantage, it is possible (but by no means trivial) to separate the beads obtained in one polymerisation reaction into a number of separate fractions such that the beads in one fraction effectively provide the same signal as each other but beads in different fractions provide signals which can be distinguished from each other by appropriately sensitive equipment. Therefore, in principle, this approach means that a single polymerisation reaction can yield two or more different fractions of labeled beads that can be distinguished from each other.

It is for example possible to sort the beads (incorporating quantum dots) obtained from one polymerisation reaction on the basis of the intensity of emission of each bead using a rapid sorting procedure such as a Fluorescence Activated Cell Sorter (FACS). Here the FACS instrument would be set to include, for example, emissions between two intensity levels and to exclude emissions above and below these levels—so-called "gating". One sorting procedure would then, for example, generate three different populations of beads. A quantity between a high and low cut-off level and two subsequent batches one above the higher cut off level and one below the lower cut-off level. However because the intensity cut-off point between one intensity level and the next is a continuum, sorting from one batch to another may result in some particles being placed in a different batch from one run to another i.e. the code fails.

This problem would be further exacerbated by the use of multiple machines where different machines will not possess exactly the same intensity calibration levels. A possible way round this problem would be to carry out a number of sorts based on intensities and simply discard particles that lie to close to a cut off point. However such an approach would be extremely time consuming (even with the phenomenal speed of FACS) and also result in the wastage of considerable amounts of materials (i.e. of encoded beads).

It is therefore an object of the present invention to obviate or mitigate the above mentioned disadvantages.

SUMMARY OF THE INVENTION

According to the present invention there is provided a labeled polymeric bead wherein individual beads comprise:

(a) a primary particle formed of a synthetic polymeric material, and (b) at least one secondary particle entrapped within the primary particle of the bead and being comprised of a synthetic polymer material incorporating reporter moieties, preferably at least around 500 reporter moieties.

Beads in accordance with the invention are capable of providing a detectable signal (generated by the reporter moieties on application of an appropriate stimulus) which is dependent on the total number of reporter moieties in the bead which in turn is dependent on the combination of:

(a) the number of secondary-particles in the primary particle; and (b) the number of types of secondary-particle in the primary particle.

As described more fully below, beads in accordance with the invention may easily be produced having different combinations of secondary-particles. Such beads (i.e. those having different combinations of secondary-particles) will contain significantly different total numbers of reporter moieties and are therefore readily distinguishable from each other.

Preferably the secondary particles include at least one reporter moiety and more preferably a plurality thereof. Generally there will be 1 to 1,000,000 secondary particles in each primary particle although more typically the number of secondary particles (per primary particle) will be 2 to 10,000, e.g. 2 to 5,000. For many embodiments of the invention there will be 5 to 100 secondary particles in each primary particle. Each secondary particle will generally contain at least around 500 reporter moieties to ensure that a detectable signal is provided by each secondary particle. Preferably each secondary particle contains at least around 750, more preferably at least 1000, and most preferably at least 10,000 reporter moieties. More preferably each secondary particle contains at least 100,000 (e.g. at least 1,000,000) reporter moieties. It can therefore easily be seen that beads containing (in the primary particle) different numbers of secondary will contain significantly different total numbers of reporter moieties so that such beads can be readily distinguished from each other.

Generally the primary particles will have a maximum cross-sectional dimension of 500 µm, e.g. 2 to 500 µm, e.g. 5 to 200 µm. Typically, the secondary particles will generally have a maximum cross-sectional dimension of 0.2 to 2 µm.

In a preferred embodiment of the invention, the reporter moieties (in the secondary particles) are quantum dots. The quantum dots may, for example, be core, core-shell or core-multi shell quantum dots. Other types of reporter moieties may for example be used, e.g. luminescent dyes, phosphors such as inorganic lanthanides, fluorescent compounds such as rhodamine, coloured/chromophoric compounds, other "up converting materials", Raman active compounds such as nitrile-containing compounds, NMR distinguishable isotopic labels such as $^{14}N/^{15}N$ nitrogen labeled compounds. With specific reference to fluorescent dyes and quantum dots, it is possible to use one tyre of dye or quantum dot which excites another type of dye or quantum dot by Fluorescence Resonance Energy Transfer (FRET). Reporter moieties can also include metallic particles/clusters (such as silver and gold particles), magnetic particles, radioisotopic labels or other compounds which possess a specific property/functionality that can be readily distinguished by a spectroscopic/analytic/non-destructive technique. An example of such a functional group containing reporter material would be an aldehyde or a nitrile both of which can be readily identified by infrared and Raman spectroscopy respectively. A further example would be a reporter material containing fluorine which can be identified by infrared and Raman spectroscopy.

The secondary particles (which are ultimately incorporated in the primary particles) may be formed by incorporating the reporter moieties in a polymerisation reaction which yields particles (e.g. having a diameter of 0.2 to 2.0 µm) incorporating the reporter moieties. Examples of polymerisation methods that may be used include suspension, dispersion, emulsion, living, anionic, cationic, RAFT, ATRP, bulk, ring closing metathesis and ring opening metathesis or else by any other method of incorporation into the polymer matrix of the larger polymeric particles. The polymerisation reaction will result in secondary particles containing statistically similar amounts of the reporter moieties.

The reporter moieties can be irreversibly incorporated in the secondary particles in a number of ways, e.g. chemical, covalent, ionic, physical (e.g. by entrapment) or any other form of interaction.

The secondary particles thus obtained can then be incorporated in a further polymerisation reaction to form primary particles incorporating a plurality of the secondary particles. Examples of polymerisation methods that may be used include suspension, dispersion, emulsion, living, anionic, cationic, RAFT, ATRP, bulk, ring closing metathesis and ring opening metathesis or else by any other method of incorporation into the polymer matrix of the larger polymeric particles.

The primary matrix of the secondary particles and/or the polymer matrix of the primary particles can be inert. Alternatively either or both matrices may be produced with a functionalised monomer. Alternatively either or both matrices may be functionalised after polymerisation.

The primary and secondary polymeric particles produced by these procedures may have any shape/morphology or 3-dimensional structure. Thus, for example, the particles may be spherical, disc-like, rod-like, ovoid, cubic or rectangular (many other configurations are also possible).

The polymerisation reaction for forming the primary particles may be effected using secondary particles of the same "type" (i.e. containing substantially the same numbers of the same reporter moieties), e.g. as obtained from a single polymerisation reaction for producing the secondary particles. For the purposes of the present invention, the term "same type" as applied to a sub-particle refers to sub-particles that contain approximately the same population of reporter moieties, i.e. within a narrowly defined distribution. Alternatively the polymerisation procedure for forming the primary particles may be effected using a mixture of different types of secondary particles, e.g. differing in numbers and/or nature of the reporter moieties.

The result of incorporating the secondary particles into the primary particles is that the resulting beads possess unique combinations of 'quanta' of one or more reporter material resulting in a distinct encoding pattern for that particular bead.

For example it is possible to mix separate batches of secondary particles containing (only) red quantum dots with batches containing further (separate) batches of secondary particles containing blue quantum dots and green quantum dots to give a population of secondary particles in the ratio of 10 blue:5 red: 1 green.

These will then be incorporated into primary particles by any suitable polymerisation reaction to generate beads (containing the secondary particles) which possess distinct readable codes/signatures for example based on the colour and intensity of the three colours/channels of QD emissions (i.e. the number/'quanta' of smaller beads of each colour within each bigger bead). Beads resulting from this procedure having differing contents of secondary particles (e.g. different numbers of any one type of secondary particle) are readily distinguished from each other because of the significantly different total number of reporter moieties present in the bead. As such, the beads from the polymerisation reaction can readily be sorted into different fractions with the beads of each fraction being essentially identical to each other in turns of their detection characteristic but readily detectably different from beads in other fractions.

Differently sized reporter material-containing secondary particles can also be used to encode the larger polymeric particles. For example some blue QD-containing secondary particles of 2 μm and some red QD-containing smaller beads of 10 μm may be incorporated into the same population of primary particles. The resulting beads may then be distinguished from one another on the basis of both the size and colour of the secondary particles they contain.

Differently shaped reporter material-containing secondary particles can also be used to encode the primary particles. For example some blue QD-containing spherical secondary particles and some red QD-containing cubic secondary particles may be incorporated into the same population of primary particles. The resulting beads may then be distinguished from one another on the basis of both the shape and colour of the secondary particles they contain.

In addition the incorporation of specifically shaped reporter material-containing secondary particles into primary particles may confer specific shape related properties e.g. a dipole moment or a diffraction property, upon the resulting bead.

The primary and/or secondary particles may be chemically inert or alternatively may be chemically reactive/functionalised. The chemical functionality may be introduced during the construction of the particle, for example by the incorporation of a chemically functionalised monomer, or alternatively chemical functionality may be introduced in a post particle construction treatment for example a chloromethylation reaction. Additionally chemical functionality may be introduced by a post particle construction polymeric graft or other similar process whereby chemically reactive polymer(s) are attached to the outer layers of the reporter material containing polymeric particles. It will be obvious to those skilled in the art that more than one such post construction derivatisation process may be carried out to introduce chemical functionality onto/into the reporter material containing polymeric particles.

Although the invention has been described with specific reference to beads comprising primary particles and secondary particles, it should be understood that other constructions are within the ambit of the invention. Thus, for example, beads in accordance with the invention may comprise primary, secondary and tertiary particles. More specifically, the tertiary particles may contain reporter moieties, the secondary particles may contain various combinations of the tertiary particles, and the primary particles contain various combinations of the secondary particles.

A further possibility is a bead comprising a primary particle incorporating one or more secondary particles (each, in turn, incorporating one or more reporter moieties) and at least one polymeric shell provided around the primary particle. Each polymeric shell may itself incorporate one or more secondary particles. Thus, for example, assume that the primary particle is spherical. In this case, there may be one or more concentric polymer outer shells provided around the primary particle, each such shell incorporating one or more secondary particles.

BRIEF DESCRIPTION OF THE DRAWINGS

The invention will be further described by way of example only with reference to the accompanying drawings in which.

DETAILED DESCRIPTION OF THE INVENTION

Figure 1:
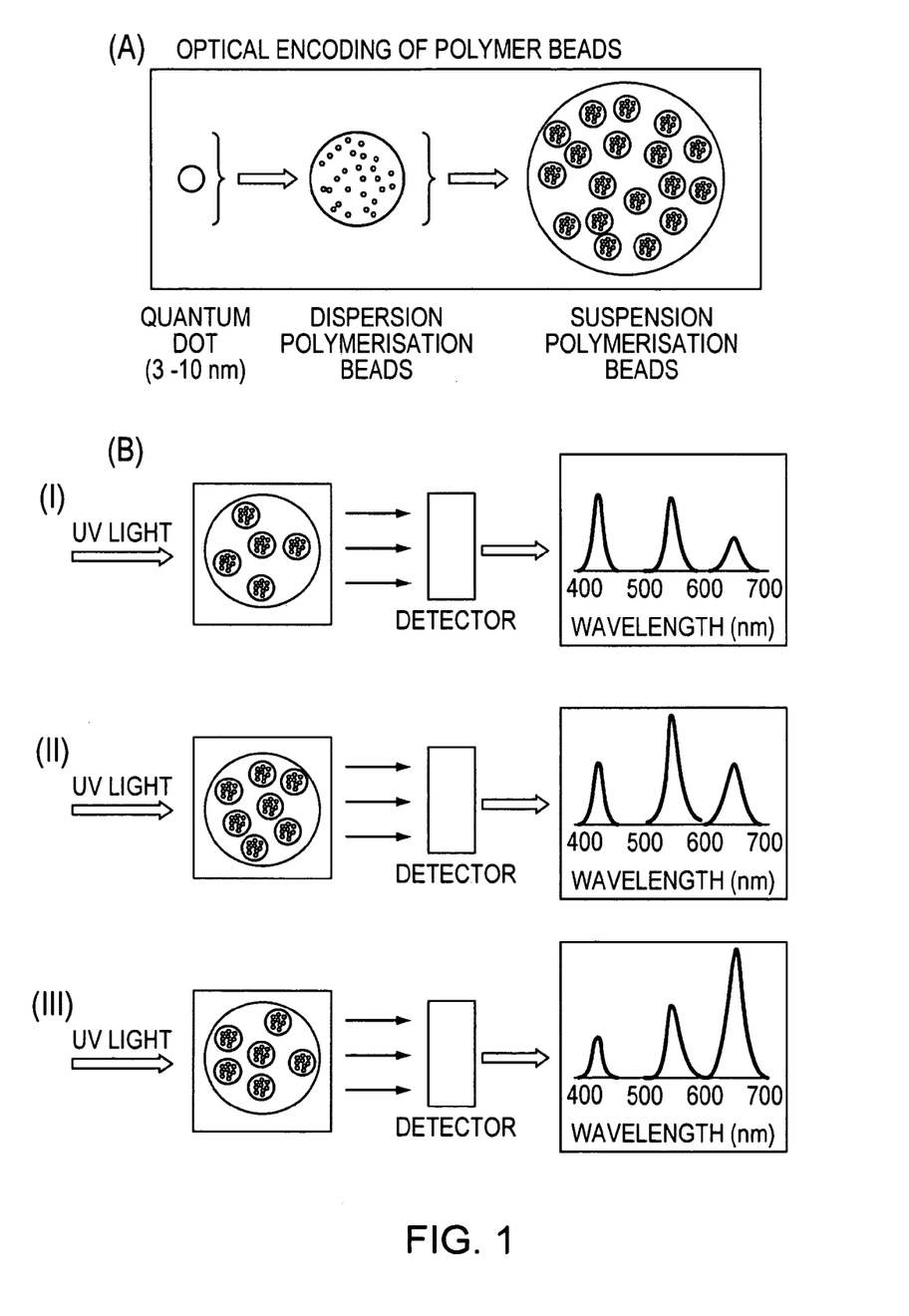
FIG. 1 schematically illustrates the structure of labeled beads in accordance with the invention and spectra obtained using examples of such particles.

Reference is made firstly to FIG. 1(A) which, at the right hand side thereof, illustrates one embodiment of a labeled bead ("Suspension Polymerisation Particle") in accordance with the invention. This particle, which may for example have a size of 5-200 μm, is comprised of a polymeric matrix in which are embedded a plurality of secondary particles ("Dispersion Polymerisation Beads") each incorporating a population of quantum dots.

Each of these secondary particles may incorporate quantum dots of a single type but the type may vary between secondary particles. Thus for example some secondary particles (the "red secondaries") may incorporate a population of quantum dots that emit red light when excited by UV radiation, some (the "blue secondaries") may incorporate quantum dots that emit blue light and others (the "green secondaries") may incorporate quantum dots that emit green light.

Secondary particles that contain the same type of quantum dot will generally all contain approximately the same number thereof. However this number may be different for quantum dots of a different type. Thus, for example, the aforementioned "red secondaries" will each contain approximately the same number of quantum dots. However the "green secondaries" may contain a significantly different number of quantum dots (although the "green secondaries" will contain approximately the same number of quantum dots as each other). Similarly for the "blue secondaries".

It will be appreciated that, to produce the illustrated labeled particle, individual collections of red, green and blue sub-particles ("secondaries") are produced by dispersion polymerisation techniques using a reagent system incorporating quantum dots of the appropriate "colour".

Fractions of red, green and blue "secondaries" are then incorporated into a suspension polymerisation procedure to produce a collection of labeled particles of the type illustrated in FIG. 1A. This collection may then be readily sorted into fractions with the members of any one fraction containing exactly the same number of the different types of sub-particle.

FIG. 1(B) illustrates how labeled beads in accordance with the invention may readily be distinguished from each other in the case where individual beads have differing contents of secondary particles.

For the purposes of the following description, the beads depicted as (i)-(iii) in FIG. 1(B) are assumed to contain the following ratios of secondary particles of the indicated type (although in practice larger numbers of the various types of secondary particles are likely to be present).

| Bead No. | Red Secondary Particles | Blue Secondary Particles | Green Secondary Particles |
|---|---|---|---|
| (i) | 1 | 2 | 2 |
| (ii) | 2 | 2 | 3 |
| (iii) | 3 | 1 | 2 |

Again for the purposes of illustration, FIG. 1(B) shows the particles (i)-(iii) being illuminated with UV light which on emission from the particle is analysed by a detector to provide the emission spectra illustrated at the right hand side of FIG. 1(B), for which blue emission is represented by the left hand peak, green emission by the middle peak and red emission by the right hand peak.

It will be appreciated from FIG. 1(B) that particle (i) has a particular emission spectrum as governed by the number of red, blue and green secondary particles present in the bead. The spectrum of particle (i) is different from that of particles (ii) and (iii) which in turn are different from each other.

Thus the individual particles (i)-(iii) are readily distinguishable from each other.

Figure 2:
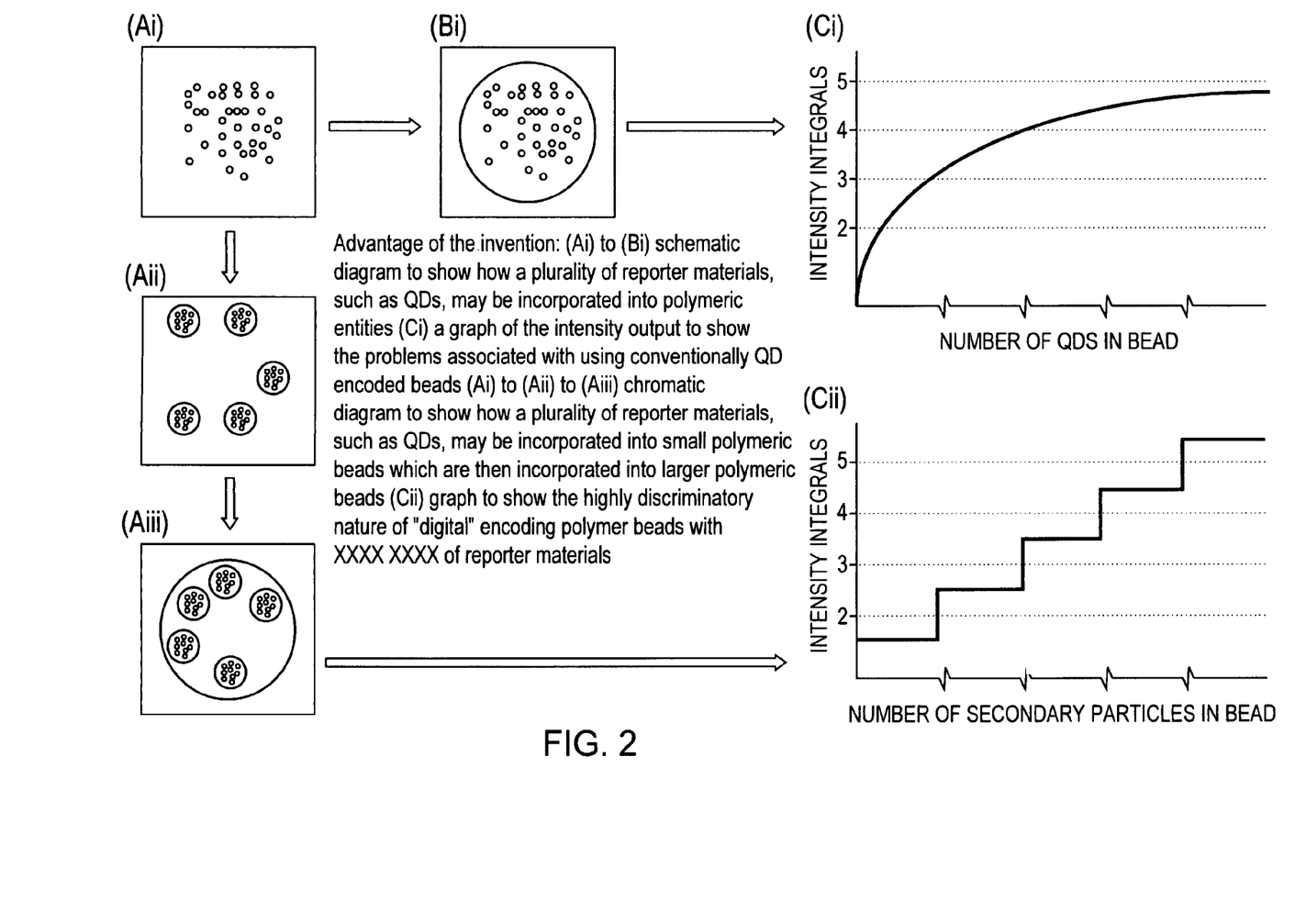
FIG. 2 schematically illustrates intensity outputs of (a) labeled beads in accordance with the invention, and (b) labeled beads of the prior art.

FIG. 2 schematically illustrates how a collection of beads in accordance with the invention in which some of the beads contain a different number of secondary particles (incorporating quantum dots as reporter moieties) than others are much more readily distinguished from each other than are labeled beads of the prior art which comprise a single particle incorporating differing numbers of reporter moieties.

More specifically, the upper graph of FIG. 2 relates to the prior art labeled beads and the lower graph relates to labeled beads of the invention. The prior art labeled beads have been produced by a suspension polymerisation reaction conducted with quantum dots which has resulted in a collection of labeled beads containing a range of individual quantum dots. The "x-axis" of the upper graph in FIG. 2 represents (going from left to right) increasing numbers of quantum dots in the individual polymer particles of the prior art beads. The "y-axis" represents intensity of emission (arbitrary units). It will be seen from the upper graph of FIG. 2 that (for the prior art particles) a plot of number of quantum dots in the (prior art) beads vs intensity is a smooth curve.

Consider now, in contrast, the lower graph of FIG. 2 which relates to labeled beads of the invention. The "x-axis" of this graph represents the number of secondary particles in the beads and the "y-axis" again represents intensity (in arbitrary units). It can be seen that, for the labeled beads of the invention, a plot of number of secondary particles vs intensity is stepped such that each additional secondary particle produces a distinct rise in the intensity of the beads.

Figure 3:
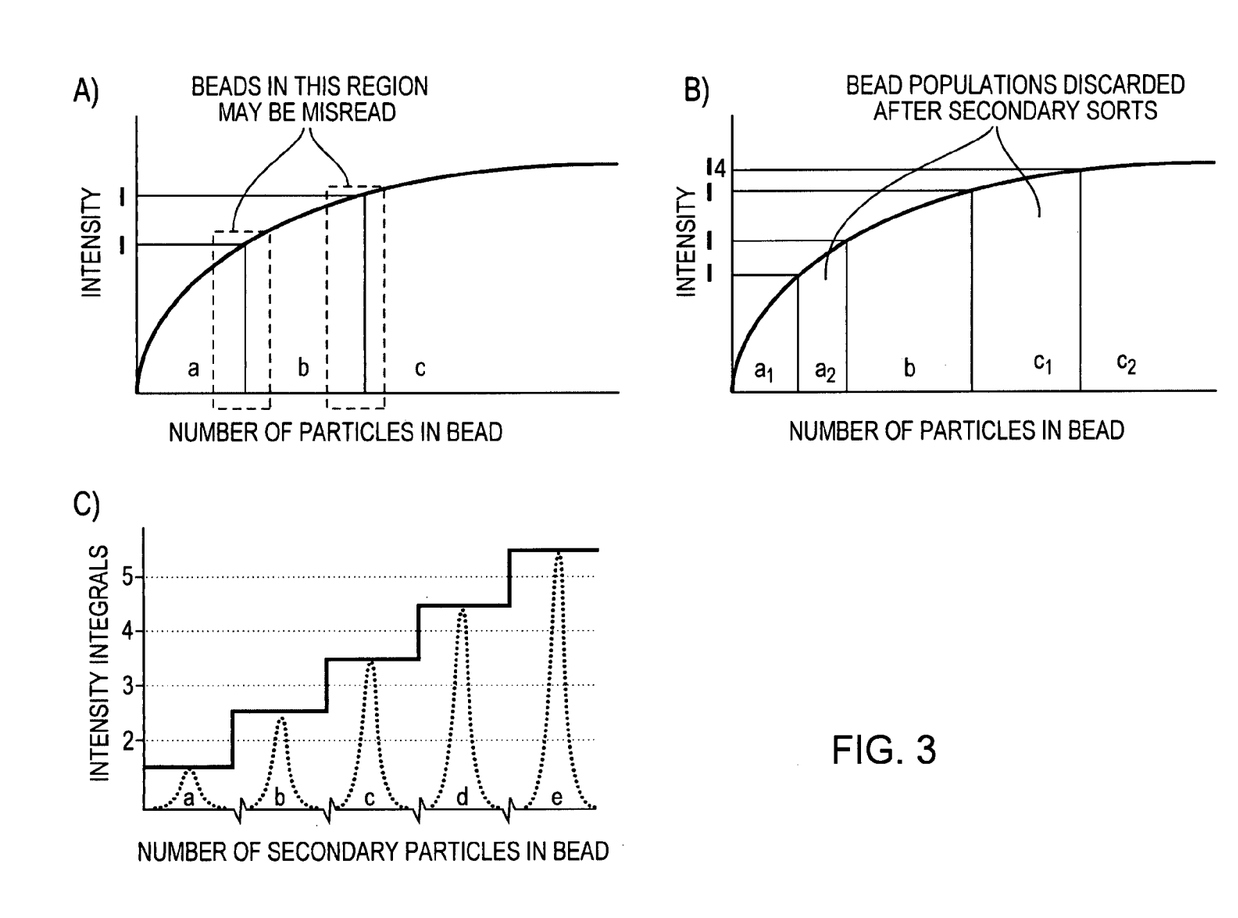
FIG. 3 schematically illustrates intensity-based sorts of (a) labeled beads in accordance with the invention, and (b) labeled beads of the prior art.
Figure 4:
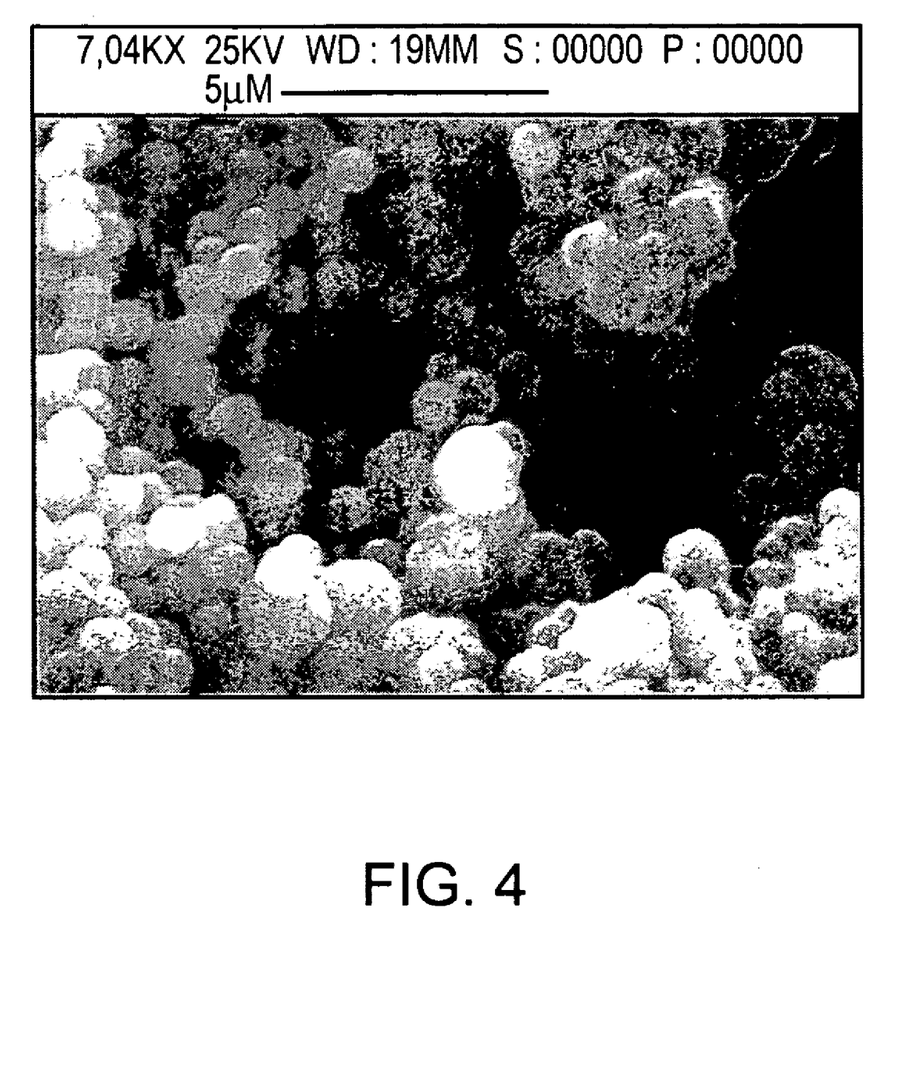
FIG. 4 is a scanning electron microscopy (SEM) image of QD-containing dispersion beads produced using the large-scale dispersion polymerisation procedure set out below.
Figure 5A:
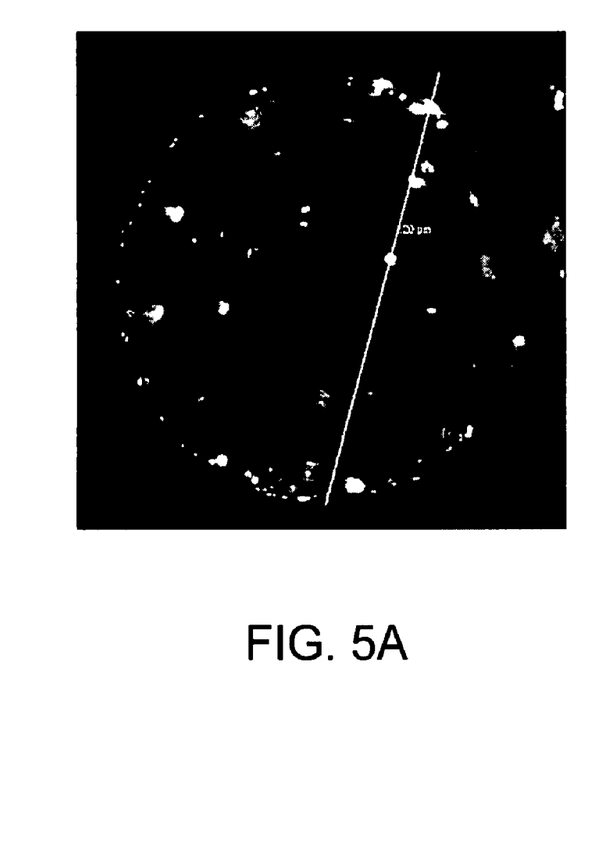
FIG. 5(a) a confocal microscope image of a suspension bead encapsulated within a thin film of PDMS.
Figure 5B:
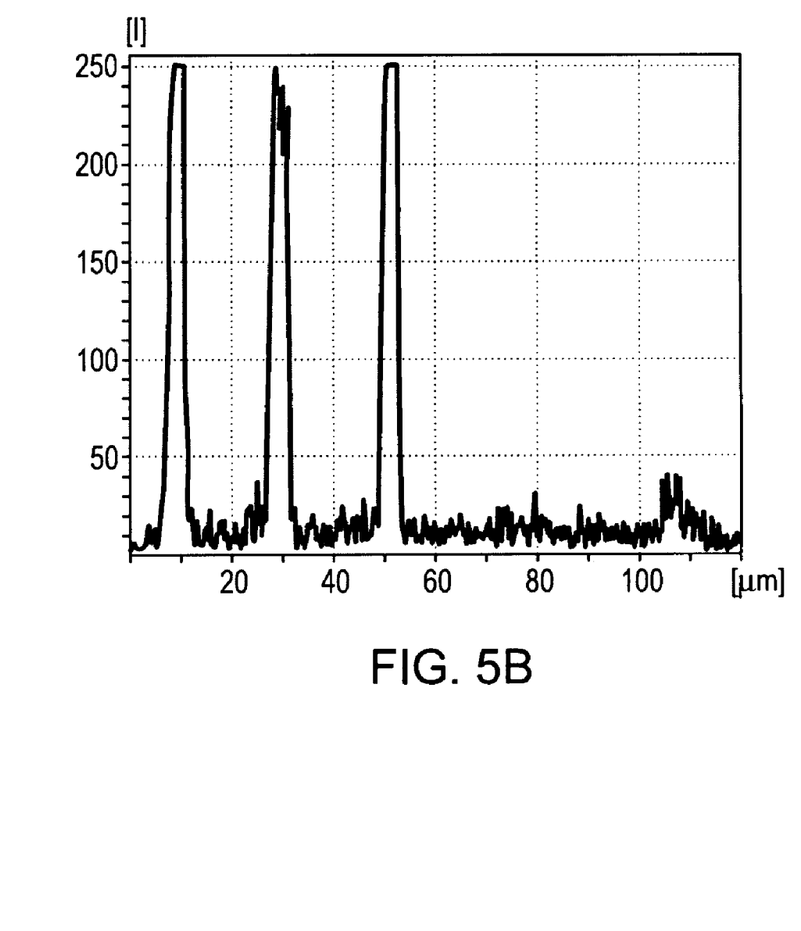
FIG. 5(b) a cross-sectional fluorescence emission fingerprint of the bead of FIG. 5(a) (fingerprint taken along the line shown in FIG. 5(a))
Figure 6:
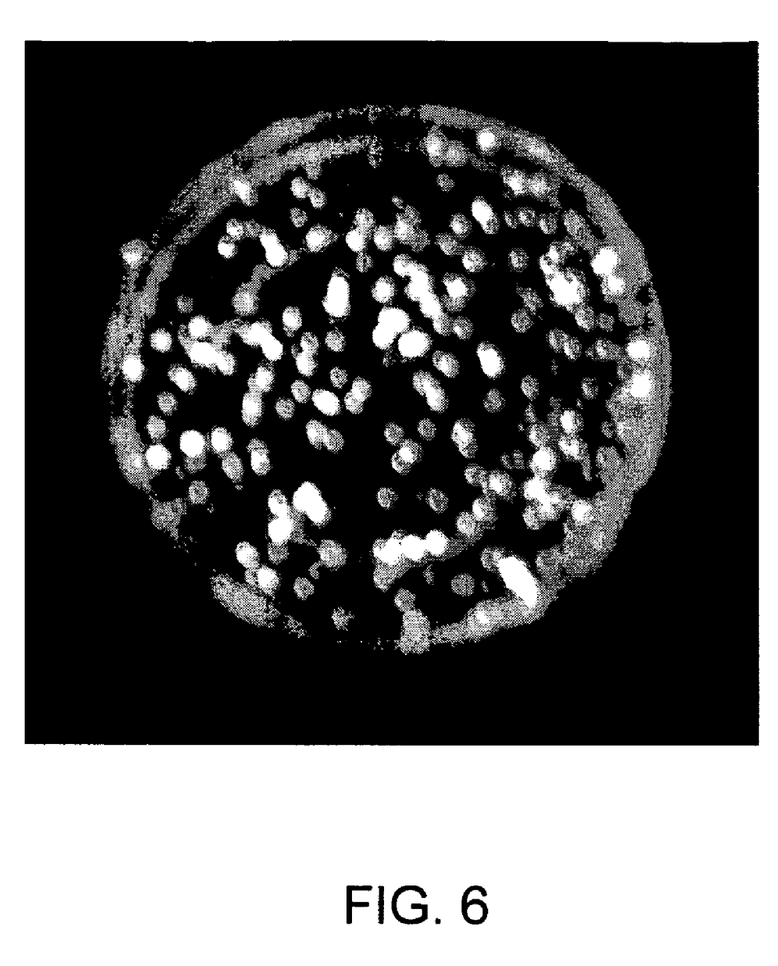
FIG. 6 is a vertical view down a PDMS-based rod that encapsulates QD-containing beads generated using a small scale suspension polymerisation reaction as set out below.
Figure 7:
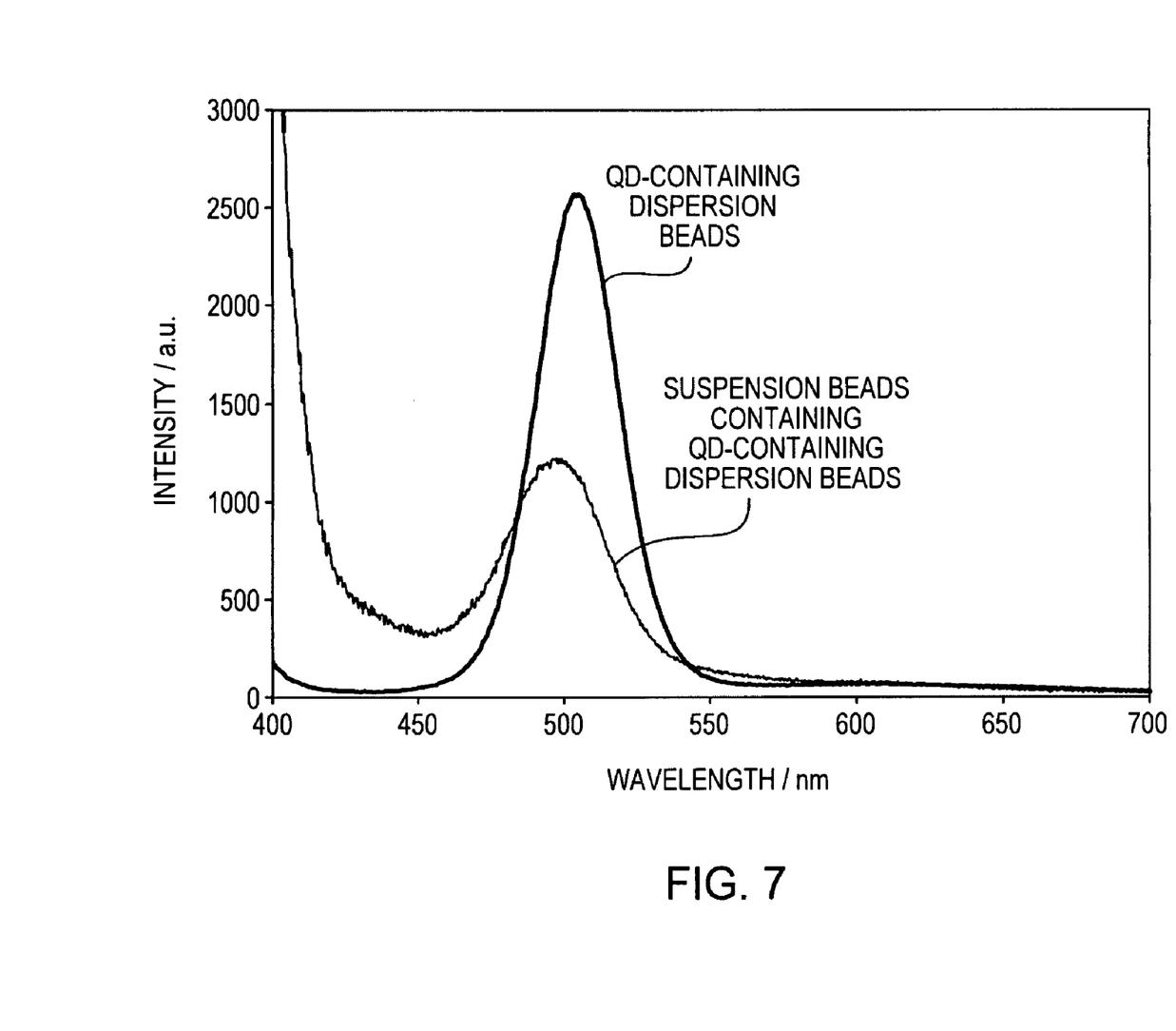
FIG. 7 shows superimposed PL spectra of a sample of QD-containing dispersion beads and a sample of suspension beads that contain the QD-containing dispersion beads.
Figure 8:
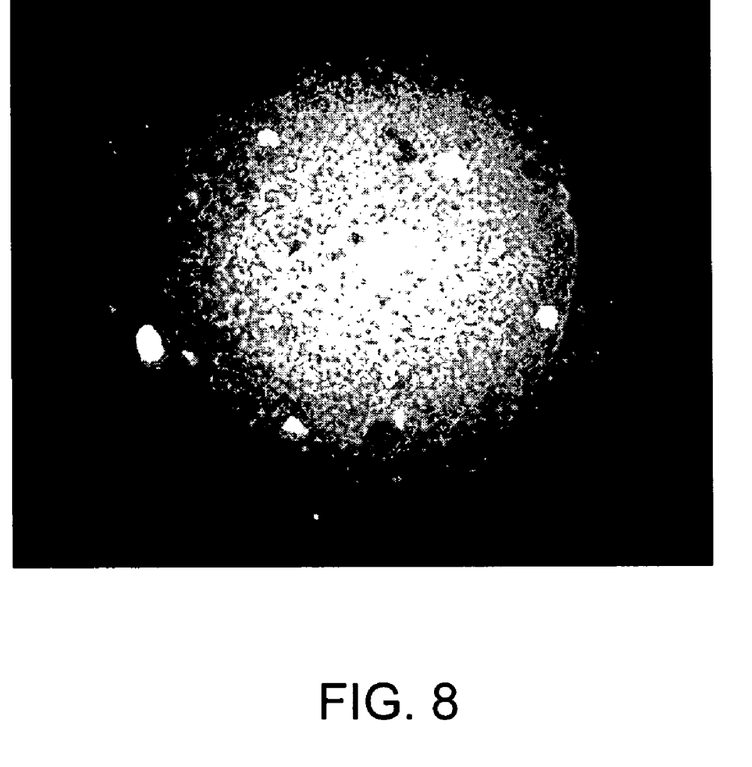
FIG. 8 is a confocal microscopy image of a bead from within a sample of suspension beads that contain the QD-containing dispersion beads (made according to entry 7 of Table 2 below).

Reference is now made to FIG. 3 which compares intensity based sorts of the prior art labeled beads and those of the invention. Graphs (A) and (B) of FIG. 3 are effectively the same plots as represented by the upper graph of FIG. 2. Graph (C) of FIG. 3 is effectively the same plot as represented by the lower graph of FIG. 2.

Assume that it is desired to sort the prior art beads into different fractions. Graph (A) represents an intensity based sort carried out at two different intensities. In principle, this gives three populations of beads a, b and c. However beads having intensities close to the "sorting intensities" may be mis-sorted if the procedure is carried out again, for example after subjecting the beads to a biological assay procedure, and the difference in emission intensity between individual beads is very small.

For the purposes of Graph (B) it is assumed that the prior art particles have initially been sorted at Intensities $I_1$ and $I_2$ into three fractions a, b and c (as represented by Graph (A)). Each fraction is now subjected to a secondary sort. More specifically, fraction a is subjected to a sort at intensity $I_3$ ($<I_1$). This sort separates fraction a into two sub-fractions $a_1$ and $a_2$. The latter fraction is then discarded.

Fraction c is subjected to a secondary sort at an intensity $I_4$ ($>I_2$) so that two sub-fractions $c_1$ and $c_2$ are generated (having intensities below and above $I_4$ respectively). Fraction $c_1$ is discarded.

Consider now the situation represented by Graph C for particles in accordance with the invention. Four primary sorts at different intensities give five distinctly different bead populations readily discriminated from one another on the basis of their quantum dot emission intensities. This procedure is highly efficient both in terms of the number of sorting procedures required and in the fact that no material need be discarded.

The invention is illustrated by the following non-limiting Examples.

EXAMPLES

1. Materials

Cadmium oxide, oleic acid, octadecene, divinylbenzene, styrene, sulfur, poly(N-vinylpyrrolidone) (PVP, molecular mass: 40,000), poly(vinyl alcohol) (PVA, molecular mass: 85,000), and 1,1'-azobis-(cyclohexanecarbonitrile) (ACHN) were purchased from Aldrich, Fisher and Lancaster and were used without any further purification. Methanol, toluene, acetone and chloroform were purchased from VWR and used as received. Deuterated chloroform was purchased from Goss Scientific and used as received.

All syntheses and manipulations were carried out under a dry oxygen-free argon or nitrogen atmosphere using standard Schlenk and glove box techniques. All solvents were analytical grade and distilled from appropriate drying agents prior to use (Na/K-benzophenone for THF, $Et_2O$, toluene, hexanes, pentane; magnesium for methanol and ethanol and calcium hydride for acetone).

2. Synthesis of CdSe/ZnS and CdSe Nanoparticles

CdSe nanoparticles were synthesized the method disclosed in WO-A-05106082. Preparation of CdSe—HDA Capped Nanoparticles Hexadecylamine HDA (500 g) was placed in a three-neck round bottomed flask and dried and degassed by heating to 120° C. under a dynamic vacuum for >1 hour. The solution was then cooled to 60° C. To this was added 0.718 g of $[HNEt_3]_4 \cdot [Cd_{10}Se_4(SPh)_{16}]$ (0.20 mmols). In total 42 mmols, 22.0 ml of TOPSe and 42 mmols, (19.5 ml, 2.15M) of $Me_2Cd.TOP$ was used. Initially 4 mmol of TOPSe and 4 mmols of $Me_2Cd.TOP$ were added to the reaction at room temperature and the temperature increased to 110° C. and allowed to stir for 2 hours. The reaction was a deep yellow colour, the temperature was progressively increased at a rate of 1° C./5 min with equimolar amounts of TOPSe and $Me_2Cd.TOP$ being added dropwise. The reaction was stopped when the PL emission maximum had reached 600 nm, by cooling to 60° C. followed by addition of 300 ml of dry ethanol or acetone. This produced a precipitation of deep red particles, which were further isolated by filtration. The resulting CdSe particles were recrystallized by re-dissolving in toluene followed by filtering through Celite followed by re-precipitation from warm ethanol to remove any excess HDA, selenium or cadmium present. This produced 10.10 g of HDA capped CdSe nanoparticles. Elemental analysis C=20.88, H=3.58, N=1.29, Cd=46.43%. Max PL=585 nm, FWHM=35 nm. 38.98 mmols, 93% of $Me_2Cd$ consumed in forming the quantum dots.

3. Preparation of CdSe/ZnS-HDA Capped Nanoparticles

HDA (800 g) was placed in a three neck round-bottom flask, dried and degassed by heating to 120° C. under a dynamic vacuum for >1 hour. The solution was then cooled to 60° C., to this was added 9.23 g of CdSe nanoparticles that have a PL maximum emission of 585 nm. The HDA was then heated to 220° C. To this was added by alternate dropwise addition a total of 20 ml of 0.5M $Me_2Zn.TOP$ and 0.5M, 20 ml of sulfur dissolved in octylamine. Three alternate additions of 3.5, 5.5 and 11.0 ml of each were made, whereby initially 3.5 ml of sulphur was added dropwise until the intensity of the PL maximum was near zero. Then 3.5 ml of $Me_2Zn.TOP$ was added dropwise until the intensity of the PL maximum had reached a maximum. This cycle was repeated with the PL maximum reaching a higher intensity with each cycle. On the last cycle, additional precursor was added once the PL maximum intensity been reached until it was between 5-10% below the maximum intensity, and the reaction was allowed to anneal at 150° C. for 1 hour. The reaction mixture was then allowed to cool to 60° C. whereupon 300 ml of dry "warm" ethanol was added which resulted in the precipitation of particles. The resulting CdSe—ZnS particles were dried before re-dissolving in toluene and filtering through Celite followed by re-precipitation from warm ethanol to remove any excess HDA. This produced 12.08 g of HDA capped CdSe—ZnS core-shell nanoparticles. Elemental analysis C=20.27, H=3.37, N=1.25, Cd=40.11, Zn=4.43%; Max PL 590 nm, FWHM 36 nm.

4. Ligand Exchange

Quantum dots were dissolved in 1,4-dioxane, 4 ml, containing a large excess of the polymerisable ligand, 1 mmol. The solution was then stirred for 20 hours at room temperature. Centrifugation and drying resulted in ligand exchanged quantum dots (14 mg for the p-vinylbenzylDOPO and 10 mg for p-octenylDOPO batches). Product structures were confirmed by $^1H$ and $^{13}C$ NMR and APCI mass spectrometry.

5. Small-Scale Suspension Polymerisation Procedure 1

Aqueous polyinylalcohol (PVA) solution (20 ml, 1% wt/wt, 87-89% hydrolyzed PVA, average MW 85,000-146,000) was prepared and transferred to the reaction vessel (screw cap boiling tube attached to a $N_2$/vacuum manifold system) and degassed with $N_2$ for 20 minutes. A monomer mixture—styrene (10 mmol), divinylbenzene and quantum dots—was prepared and stirred for 5 minutes. AIBN (76 μmol) was added to the monomer mixture then the resultant mixture was stirred for a further 15 minutes with $N_2$ degassing. The dark orange monomer solution (colour due to the quantum dots) was added to the PVA solution while rapidly stirring with a cross-shaped magnetic stirrer. A two phase system resulted with orange droplets being suspended in the colourless aqueous PVA solution. The suspension was stirred at room temperature for 30 minutes before the temperature was increased to 70° C. and stirring was continued for a further 4 hours. The resin beads were then collected over a 38 μm sieve and washed in situ with copious amounts of water. The damp beads were then transferred to a sintered funnel and washed with methanol (100 $cm^3$), MeOH/THF, 1/1 (100 $cm^3$), THF (100 $cm^3$), $CH_2Cl_2$ (100 $cm^3$) and acetone (100 $cm^3$).

6. Small-Scale Dispersion Polymerisation Procedure 2

A reaction medium comprising poly(N-vinylpyrrolidone), average MW 55000, (0.2 g) dissolved in a 95:5 ethanol:water mixture (10 ml) was placed in a reaction tube of a 12-place stirring carousel. To this reaction medium was added a monomer mixture comprised of 10 mmol of monomer/crosslinker in total. By way of example (entry 5 below) the monomer comprised of styrene (2 mmol), divinylbenzene (8 mmol) AIBN (0.01 g) and quantum dots (5 mg). Nitrogen was then bubbled though the resultant mixture for 20 minutes and the solution kept under a nitrogen atmosphere until the reaction had proceeded to completion. The solution was gently stirred (approximately 150 rpm) and brought to and maintained at a temperature of 60° C. for 16 hours. The beads were then collected and washed by centrifugation

TABLE 1

| Entry | Monomers | Quantum Dot | Reaction Scale | PL λmax; intensity |
|---|---|---|---|---|
| 1 | S/DVB 100/0 | 5 mg CdSe/ZnS; 590 nm | 10 ml | 570; 2200 |
| 2 | S/DVB (98/2) | 5 mg CdSe/ZnS; 590 nm | 10 ml | 564; 3400 |
| 3 | S/DVB (98/2) | 5 mg QDQW ZnS/CdSe/ZnS; 494 nm | 10 ml | 506; 2570 |
| 4 | S/DVB (0:100) | 5 mg QDQW ZnS/CdSe/ZnS; 494 nm | 10 ml | 506; 3334 |
| 5 | S/DVB (20:80) | 5 mg QDQW ZnS/CdSe/ZnS; 494 nm | 10 ml | 506; 3906 |
| 6 | S/DVB (40:60) | 5 mg QDQW ZnS/CdSe/ZnS; 494 nm | 10 ml | 504; 2147 |

Representative examples of quantum dot-containing beads made according to the above "Small-scale dispersion polymerisation procedure 2" and associated PL data. (S-styrene; DVB-divinylbenzene and DOPO-dioctylphosphine oxide)

7. Large-Scale Dispersion Polymerisation Procedure

Styrene (481 mmoles, 55 cm$^3$), divinylbenzene (9.0 mmoles, 1.37 ml), AIBN (3.0 mmoles, 0.5 g) and CdSe/ZnS (hexadecylamine ligand) quantum dots (100 mg) were mixed together. This mixture was then added to a reaction medium comprising poly(N-vinylpyrrolidone), average MW 55000, (10 g) dissolved in a 95:5 ethanol:water mixture (500 ml). Nitrogen was then bubbled though the resultant mixture for 20 minutes and the solution kept under a nitrogen atmosphere until the reaction had proceeded to completion. The solution was gently stirred (approximately 150 rpm) and brought to and maintained at a temperature of 60° C. for 24 hours. The beads were then collected and washed by centrifugation.

8. Procedure for Encapsulating QDs and QD-Containing Beads in Polydimethylsiloxane (PDMS)-Based Films and Rods PDMS (Sylgard 184, Dow Corning) was mixed and prepared as per the manufacturer's instructions, i.e. 10 parts base were mixed with 1 part curing agent and this mixture was then placed under high vacuum until any bubbles had been removed. A small amount of QDs or QD-containing beads (produced by a dispersion or suspension polymerisation reaction) was then added to the PDMS mixture (~1 mg in 1 ml). The resultant mixture was stirred thoroughly and again placed under high vacuum to remove any bubbles.

Thin films were prepared on a microscope slide, by either spreading the PDMS preparation with a spatula or else by placing a drop of the PDMS preparation onto a slide and pressing a cover slip on top. Thin films prepared by either of these two methods were then heated in an oven at 100° C. for 1 hour. Thicker films could similarly be prepared by pouring the liquid PDMS preparation into a suitable mould, e.g. a petri dish, and heating the PDMS preparation in situ at 100° C. Rods were prepared by pouring the PDMS preparation into a glass vial (1 cm diameter×5 cm high) and heating the PDMS preparation in situ at 100° C. for 1 hour.

9. Synthesis of Quantum Dot Doped Polystyrene Beads

CdS doped polystyrene latexes were synthesized via a modification of the suspension polymerization method. PVP (0.25 g) as the stabilizer was first dissolved in 40 ml PVA aqueous solution (wt 10%). The mixture was heated to 50° C. under $N_2$ and a solution of CdS nanoparticles (25 mg), divinylbenzene (20 mg) and ACHN (25 mg) in styrene monomer (2.5 g) was injected into the reaction mixture with vigorous stirring. The reaction was kept at 70° C. for 6 hours. After cooling to room temperature, the solution was purified by centrifugation and redispersion with toluene and water using the method previously described. The size of polymer latexes is strongly dependent on the stirring speed and PVP concentration. With this method, particles with a size range from 100 nm to 500 µm could be obtained.

10. Preparation of the Beads Containing the Quantum Dot-Containing Beads

A small scale suspension polymerisation reaction procedure was carried out exactly as described above with styrene (8 mmol) and divinyl benzene (2 mmol) as the monomer phase (10 mmol in total) and AIBN (76 µmol). The only difference in the procedure employed was that an aliquot of QD-containing dispersion beads (6.5 mg) were added to the monomer mixture, in place of QDs, just prior to the addition of the AIBN.

In addition it was possible to use this method with other ratios of styrene and divinylbenzene and also other monomers in place of styrene and divinylbenzene as the following Table indicates. In all instances the total number of moles in the monomer phase was 10 mmol.

TABLE 2

| Entry | Suspension Monomers | Dispersion Beads (made according to Table 1 entry 3) | PL of the beads containing the quantum dot-containing beads λmax; intensity |
|---|---|---|---|
| 1 | S/DVB 99/1 | 5 mg (494 nm); S/DVB, 99:1 | beads 496; 2592 |
| 2 | S/DVB 98/2 | 5 mg (494 nm); S/DVB, 99:1 | beads 496; 3267 |
| 3 | S/DVB 80/20 | 5 mg (494 nm); S/DVB, 99:1 | beads 487; 892 |
| 4 | S/DVB 60/40 | 5 mg (494 nm); S/DVB, 99:1 | beads 487; 1113 |
| 5 | S/DVB 0/100 | 5 mg (494 nm); S/DVB, 99:1 | beads 487; 3313 |
| 6 | MMA/EGDM 99/1 | 5 mg (494 nm); S/DVB, 99:1 | beads 496; 1391 |

TABLE 2-continued

| Entry | Suspension Monomers | Dispersion Beads (made according to Table 1 entry 3) | PL of the beads containing the quantum dot-containing beads λmax; intensity |
|---|---|---|---|
| 7 | MMA/EGDM 98/2 | 5 mg (494 nm); S/DVB, 99:1 | beads 498; 3334 |
| 8 | MMA/EGDM 80/20 | 5 mg (494 nm); S/DVB, 99:1 | beads 498; 2030 |
| 9 | MMA/EGDM 60/40 | 5 mg (494 nm); S/DVB, 99:1 | beads 499; 1130 |
| 10 | MMA/EGDM 0/100 | 5 mg (494 nm); S/DVB, 99:1 | beads 498; 1739 |

Representative examples of beads that contain quantum dot-containing beads made according to the "Preparation of beads containing the quantum dot-containing beads" procedure and associated PL data. (S—styrene; DVB—divinylbenzene; MMA—methyl methacrylate; EGDM—ethylene glycol dimethacrylate).

What is claimed is:

1. A labeled polymeric bead wherein individual beads comprise:
   (a) a primary particle formed of a synthetic polymeric material, and
   (b) at least one secondary particle wholly contained within the primary particle of the bead and being comprised of a synthetic polymer material incorporating at least around 500 reporter moieties.

2. A bead as claimed in claim 1 wherein the primary particle has a maximum cross-sectional dimension of 500 μm.

3. A bead as claimed in claim 2 wherein the primary particle has a maximum cross-sectional dimension of 5 to 200 μm.

4. A bead as claimed in claim 1 wherein the at least one secondary particle has a maximum cross-sectional dimension of 0.2 to 2 μm.

5. A bead as claimed in claim 1 wherein the primary particle includes a plurality of secondary particles.

6. A bead as claimed claim 1 wherein the primary particle contains 1 to 10,000 of the secondary particles.

7. A bead as claimed in claim 6 wherein the primary particle contains 1 to 5000 of the secondary particles.

8. A bead as claimed in claim 7 wherein the primary particle contains 5 to 100 of the secondary particles.

9. A bead as claimed in claim 8 wherein the primary particle contains 20 to 50 of the secondary particles.

10. A bead as claimed in claim 1 wherein the number of reporter moieties in each secondary particle contained within a primary particle of a bead is at least around 750.

11. A bead as claimed in claim 1 wherein the number of reporter moieties in each secondary particle contained within a primary particle of a bead is at least 1000.

12. A bead as claimed in claim 1 wherein the number of reporter moieties in each secondary particle contained within a primary particle of a bead is at least 10,000.

13. A bead as claimed in claim 1 wherein the number of reporter moieties in each secondary particle contained within a primary particle of a bead is at least 100,000.

14. A bead as claimed in claim 1 wherein the reporter moieties are covalently incorporated in the secondary particles.

15. A bead as claimed in claim 1 wherein the reporter moieties are quantum dots.

16. A collection of beads as claimed in claim 1.

17. A collection as claimed in claim 16 wherein individual beads contain the same number of the same type of secondary particles.

18. A collection as claimed in claim 16 comprising beads containing different combinations of secondary particles.

19. A method of producing a collection of labeled beads comprising:
   (i) providing at least one secondary particle comprised of a synthetic polymer material incorporating a plurality of reporter moieties; and
   (ii) effecting polymerisation of a polymerisable monomer in the presence of said at least one secondary particle to form a collection of beads each comprised of a primary particle wholly containing at least one of said secondary particles.

20. A method as claimed in claim 19, wherein each secondary particle incorporates at least around 500 reporter moieties.

* * * * *